US006956476B2

(12) United States Patent
Buess et al.

(10) Patent No.: US 6,956,476 B2
(45) Date of Patent: Oct. 18, 2005

(54) METHOD AND APPARATUS FOR DETECTING A TARGET MATERIAL IN A SAMPLE BY PRE-SCREENING THE SAMPLE FOR PIEZOELECTRIC RESONANCE

(75) Inventors: Michael L. Buess, Alexandria, VA (US); Allen M. Garroway, Fort Washington, MD (US); Joel B. Miller, Cheverly, MD (US); James P. Yesinowski, Fort Washington, MD (US); Roy P. Lindquist, Oakton, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/166,287

(22) Filed: Jun. 5, 2002

(65) Prior Publication Data

US 2003/0001570 A1    Jan. 2, 2003

Related U.S. Application Data

(62) Division of application No. 08/869,934, filed on Jun. 5, 1997, now Pat. No. 6,411,208.

(51) Int. Cl.[7] .............................................. G08B 21/00
(52) U.S. Cl. ...................................... 340/540; 324/309
(58) Field of Search ....................... 340/540; 324/300, 324/309, 314, 318

(56) References Cited

U.S. PATENT DOCUMENTS

| 4,170,144 A | | 10/1979 | Scott |
| 4,511,998 A | | 4/1985 | Kanda et al. |
| 4,636,730 A | * | 1/1987 | Bottomley ................... 324/322 |
| 4,833,392 A | * | 5/1989 | Hahn et al. ................... 324/313 |
| 4,887,034 A | | 12/1989 | Smith |
| 5,006,805 A | * | 4/1991 | Ingwersen ................... 324/322 |
| 5,159,617 A | | 10/1992 | King et al. |
| 5,166,615 A | | 11/1992 | Sidles |
| 5,190,766 A | | 3/1993 | Ishihara |
| 5,206,592 A | | 4/1993 | Buess et al. |
| 5,233,300 A | | 8/1993 | Buess et al. |

(Continued)

FOREIGN PATENT DOCUMENTS

WO    WO 93/11441    6/1993

OTHER PUBLICATIONS

K. Fosshein et al, "Dynamic Polarization Echoes In Piezoelectric Powders", Physical Review, vol. 17 No. 3, Feb. 1, 1978.

(Continued)

*Primary Examiner*—John Tweel, Jr.
(74) *Attorney, Agent, or Firm*—John J. Karasek; Stephen T. Hunnius; Amy Ressing

(57) ABSTRACT

A method and apparatus for screening samples to determine which samples include a target material. Generally, the samples are pre-screened to determine which of the samples have a piezoelectric resonance when irradiated with an electric field, to thereby indicate the presence of the target material. The samples that have the piezoelectric resonance are then further screened by a different process to confirm the presence of the target material. For example, samples that have the piezoelectric resonance are further screened for a specific nuclear quadrupole resonance (NQR), a specific nuclear magnetic resonance (NMR) or a specific visual characteristic, to confirm the presence of the target material in the sample. The apparatus and method can be used, for example, to search luggage at ports of entry for the presence of cocaine hydrochloride or heroin hydrochloride.

4 Claims, 7 Drawing Sheets

U.S. PATENT DOCUMENTS

| | | | |
|---|---|---|---|
| 5,365,171 | A | 11/1994 | Buess et al. |
| 5,424,645 | A | 6/1995 | Doty |
| 5,500,591 | A | 3/1996 | Smith et al. |
| 5,583,437 | A | 12/1996 | Smith et al. |
| 5,592,083 | A * | 1/1997 | Magnuson et al. ......... 324/300 |
| 5,608,321 | A | 3/1997 | Garroway et al. |
| 6,054,856 | A * | 4/2000 | Garroway et al. .......... 324/318 |
| 6,166,541 | A * | 12/2000 | Smith et al. ................ 324/300 |
| 6,486,838 | B1 * | 11/2002 | Smith et al. ................ 343/703 |

OTHER PUBLICATIONS

D.G. Hughes et al, "Spurious Signals Caused By The Piezoelectric Ringing Of NaNO2 in Pulsed NMR", Academic Press (1984).

James P. Yesinowski et al, "Detection of 14N and 35Cl in Cocaine Base and Hyrdrochloride Using NQR, NMR, and SQUID Techniques", Analytical Chemistry, vol. 67 No. 13. Jul. 1, 1995.

Joon C. Herl et al, "Electric Rield Effect on 14N NQR and Piezoelectric Resonance in (CH2)6N4 Powder", Ferroelectrics Letters, vol. 18, pp. 197-202, 1994.

A.A. V. Gibson et al, "Proton NMR and Piezoelectricity in Tetramethylammonium Chloride", Chemical Physic, vol. 57 No. 11, Dec. 1972.

K. Choi et al, "Inductive Detection of Piezoelectric Resonance by Using a Pulse NMR/NQR Spectrometer", Rev. Sci. Instrum. 60(10) Oct. 1989.

* cited by examiner

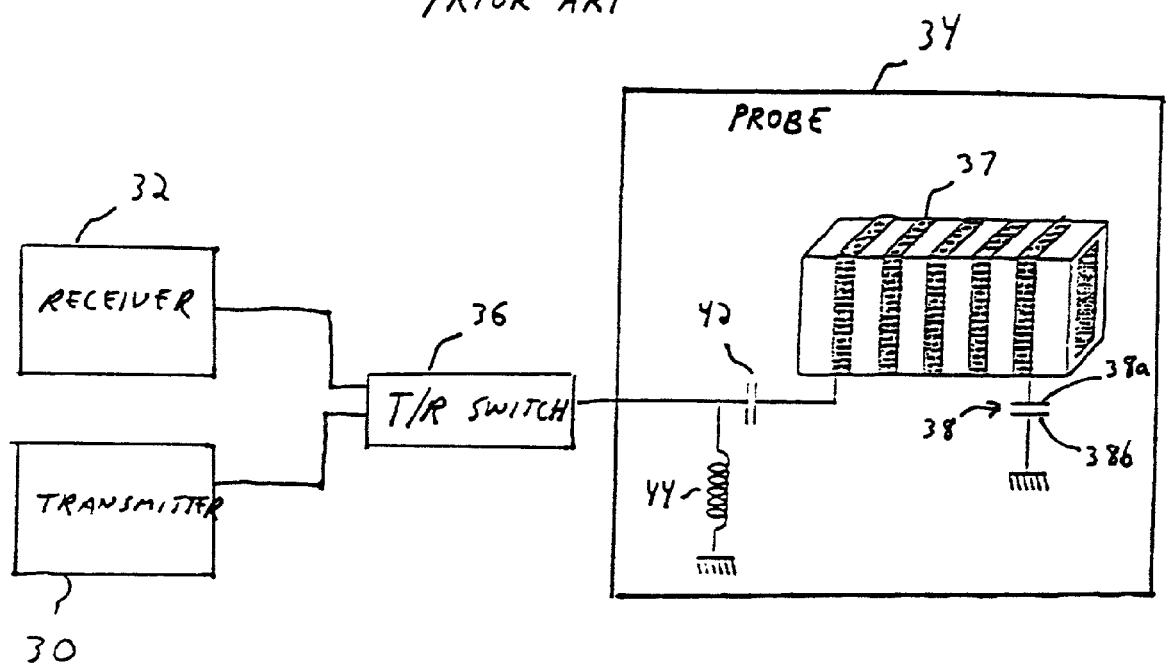

METHOD AND APPARATUS FOR DETECTING A TARGET MATERIAL IN A SAMPLE BY PRE-SCREENING THE SAMPLE FOR PIEZOELECTRIC RESONANCE

CROSS REFERENCE TO RELATED APPLICATION

This application is a divisional application of application Ser. No. 08/869,934 filed Jun. 5, 1997 U.S. Pat. No. 6,411,208.

BACKGROUND OF THE INVENTION

1. Field of the Invention

The present invention relates to a method and apparatus for determining which samples of a plurality of samples include one or more of a class of target materials. More specifically, the present invention relates to a method and apparatus which pre-screens the samples to determine which samples produce a piezoelectric resonance signal indicating the potential presence of the target material. For each sample producing the piezoelectric resonance signal, an additional detection process, such as nuclear quadrupole resonance, nuclear magnetic resonance, x-ray, canine, or manual inspection can be used to confirm the presence of the target material.

2. Description of the Related Art

There are many situations where it is desirable to detect the presence of a target material (that is, a specific substance). For example, with the unfortunate increase in drug trafficking and terrorist use of high explosives in aircraft and buildings, detection systems are often used to detect sub-kilogram quantities of narcotics and explosives against a background of more benign materials. For example, such a detection system currently is being used in airports on an experimental basis to detect narcotics or explosives hidden in luggage.

Nuclear quadrupole resonance (NQR) is a known technique for detecting a target material. Generally, radio frequency (RF) radiation at a particular frequency will induce a detectable precession in nuclei in specific substances, but not in other substances. Nuclear quadrupole resonance (NQR) takes advantage of this phenomenon to detect one of these specific substances as a target material.

FIG. 1 is a diagram illustrating a conventional NQR apparatus. Referring now to FIG. 1, a transmitter 20 and a receiver 22 are connected to a probe 24 through a transmit/receive (T/R) switch 26. Probe 24 includes a coil (not illustrated) forming part of a resonant circuit (not illustrated). To detect the presence of a target material, T/R switch 26 connects transmitter 20 to probe 24 while disconnecting receiver 22 from probe 24. Then, transmitter 20 generates a pulse and supplies the pulse to probe 24. Generally, the pulse is formed by a signal having a frequency corresponding to the resonance signal of the nuclei of the target material which is intended to be detected. Probe 24 receives the pulse, which causes the coil in probe 24 to store (RF) energy. If a sample (not illustrated) is appropriately placed near the coil, the stored RF energy will cause a corresponding electromagnetic field to irradiate the sample. If the sample includes the target material, the electromagnetic field may induce a nuclear quadrupole resonance signal in the target material.

After the sample is irradiated with the electromagnetic field, T/R switch 26 connects receiver 22 to probe 24 while disconnecting transmitter 20 from probe 24. The coil in probe 24 then detects the nuclear quadrupole resonance signal from the target material, and probe 24 produces a corresponding output signal. The output signal of probe 24 is received and analyzed by receiver 22, to confirm the presence of the target material in the sample.

NQR detection systems for the detection of explosives and narcotics are disclosed in U.S. patent titled "DETECTION OF EXPLOSIVE AND NARCOTICS BY LOW POWER LARGE SAMPLE VOLUME NUCLEAR QUADRUPOLE RESONANCE (NQR)", U.S. Pat. No. 5,233,300; U.S. patent titled "REMOVING THE EFFECTS OF ACOUSTIC RINGING AND REDUCING TEMPERATURE EFFECTS IN THE DETECTION OF EXPLOSIVES BY NQR", U.S. Pat. No. 5,365,171; U.S. patent titled "DETECTION OF EXPLOSIVES BY NUCLEAR QUADRUPOLE RESONANCE", U.S. Pat. No. 5,206,592, and "A MEANS FOR DETECTING EXPLOSIVES AND NARCOTICS BY STOCHASTIC NUCLEAR QUADRUPOLE RESONANCE (NQR)" U.S. Pat. No. 5,608,321 which are incorporated herein by reference.

Nuclear magnetic resonance (NMR) is an additional, known technique for detecting a target material. In NMR, a sample is placed in a static (or constant) magnetic field, and irradiated with rf magnetic field as in NQR. If the sample includes the target material, the rf field, under the right conditions, will cause a nuclear magnetic resonance signal to be induced in the target material. The nuclear magnetic resonance signal is then detected, to indicate the presence of the target material in the sample. For example, an NMR detection system is disclosed in U.S. patent titled "SYSTEM FOR DETECTING NUCLEAR MAGNETIC RESONANCE SIGNALS FROM SMALL SAMPLES", U.S. Pat. No. 5,166,615, which is incorporated herein by reference.

Therefore, FIG. 1 can also be used to describe a conventional NMR apparatus, with the addition of a magnet (not shown). Referring now to FIG. 1, to induce a magnetic resonance signal in a sample, T/R switch 26 connects transmitter 20 to probe 24 while disconnecting receiver 22 from probe 24. Then, transmitter 20 generates a pulse and supplies the pulse to probe 24 in the static magnetic field. Probe 24 receives the pulse, and produces a corresponding rf magnetic field. A sample (not illustrated) is then placed near probe 24 to be irradiated with the rf magnetic field. If the sample includes the target material, the rf magnetic field may induce a nuclear magnetic resonance signal in the target material.

After the sample is irradiated with the magnetic field, T/R switch 26 connects receiver 22 to probe 24 while disconnecting transmitter 20 from probe 24. Probe 24 then detects the nuclear magnetic resonance signal induced in the target material, and probe 24 produces a corresponding output signal. The output signal of probe 24 is received and analyzed by receiver 22, to confirm the presence of the target material in the sample. Multiple repetitions (scans) are also possible. Therefore, NMR is similar to NQR in that a resonance signal is induced in the target material, and the resonance signal is then detected. Unfortunately, such apparatuses are expensive and the weak NQR/NMR signals may provide slow detection of a target material.

SUMMARY OF THE INVENTION

Accordingly, it is an object of the present invention to provide a method and apparatus for detecting a target material in a sample, and which is relatively inexpensive and provides quick detection.

It is also an object of the present invention to provide a method and apparatus for determining which samples of a plurality of samples may include a target material, wherein the method and apparatus are relatively inexpensive and provide quick detection.

Additional objects and advantages of the invention will be set forth in part in the description which follows, and, in part, will be obvious from the description, or maybe learned by practice of the invention.

The foregoing objects of the present invention are achieved by providing a method including the step of detecting piezoelectric resonance in cocaine hydrochloride.

Additional objects of the present invention are achieved by providing a method of detecting the presence of a target material in a sample, the target material having a unit cell structure lacking an inversion center of symmetry leading to piezoelectric resonance when irradiated with an electric field. The method includes the steps of (a) irradiating the sample with an alternating (AC) electric field at radiofrequencies which induces the piezoelectric resonance in the target material; and (b) detecting the induced piezoelectric resonance, to thereby detect the presence of the target material in the sample.

Objects of the present invention are further achieved by providing a method of determining which samples of a plurality of samples include a target material, wherein the target material has first and second characteristics. The first characteristic is that the target material has a piezoelectric resonance when irradiated with an electric field. The second characteristic is that the target material has some other property, such as an NMR or NQR signature, that permits the specific identification of a sample containing the target material. The method includes the steps of (a) determining which samples indicate the presence of the first characteristic, to thereby determine which samples indicate the presence of the target material; and (b) for each sample determined to indicate the presence of the first characteristic, determining which of the samples indicate the presence of the second characteristic, to thereby confirm which samples include the target material.

Objects of the present invention are also achieved by providing a method of screening samples, including the steps of (a) determining which of the samples has a piezoelectric resonance when irradiated with an electric field; and (b) for each sample determined to have a piezoelectric resonance, determining which of the samples have a specific nuclear quadrupole resonance when irradiated with an electromagnetic field.

Objects of the present invention are further achieved by providing a probe which includes a capacitor. The capacitor includes first and second plates separated from each other with an electric field being formed between the first and second plates. A sample is positioned between the first and second plates so that the electric field induces a resonance signal in the sample and so that the probe detects the induced resonance signal.

BRIEF DESCRIPTION OF THE DRAWINGS

These and other objects and advantages of the invention will become apparent and readily appreciated from the following description of the preferred embodiments, taken in conjunction with the accompanying drawings of which:

FIG. 3(A) (prior art) is a diagram illustrating a probe for use in the apparatus of FIG. 2.

DESCRIPTION OF THE PREFERRED EMBODIMENTS

Figure 1:
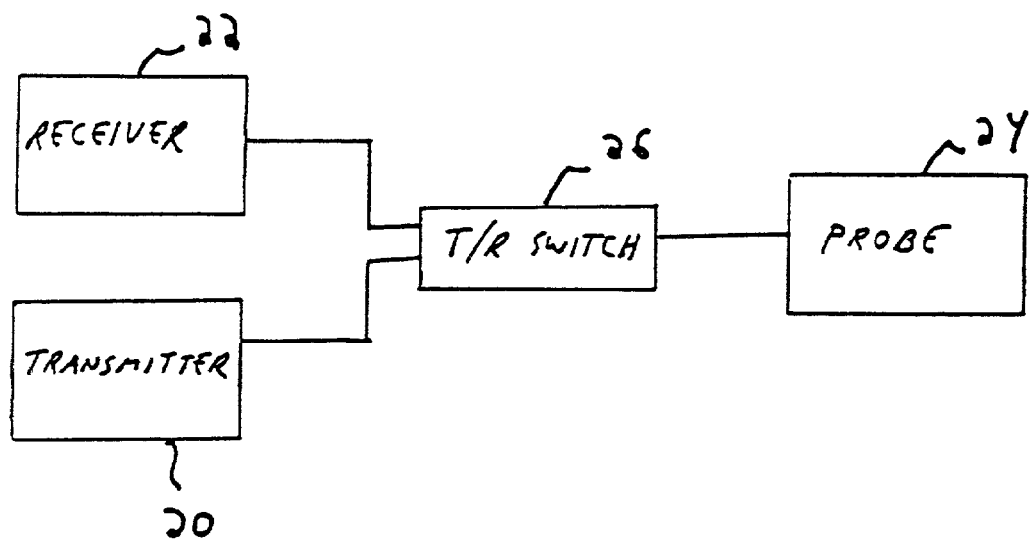
FIG. 1 (prior art) is a diagram illustrating a conventional NQR or NMR apparatus.

Reference will now be made in detail to the present preferred embodiments of the present invention, examples of which are illustrated in the accompanying drawings, wherein like reference numerals refer to like elements throughout.

Piezoelectric resonance is a well-known phenomenon which occurs in various materials. Generally, it is known that, for specific substances, an electric field applied to the substance will induce a net electric polarization in molecules of the substance. This may also be observed in ionic substances. In an alternating electric field, the resulting oscillating electric dipoles can couple mechanically to the lattice of the molecules, inducing acoustic energy, or acoustic waves, at the frequency of the applied electric field. These acoustic waves will interfere constructively and destructively, depending on the frequency of the applied electric field, the geometry of the substance, and the domain structure. A resulting mechanical resonance will favor some frequencies and suppress others. Even after the applied electric field is turned OFF, the mechanical resonance can persist for a time period typically on the order of a millisecond. By reciprocity, the acoustic waves will induce an oscillating electric polarization that can be detected, for example, by a capacitor tuned near the frequency of the applied electric field. Therefore, it is known that certain substances exhibit a piezoelectric resonance signal when irradiated with an electric field.

Piezoelectric resonance is disclosed, for example, in K. Choi and I. Yu, "INDUCTIVE DETECTION OF PIEZOELECTRIC RESONANCE BY USING A PULSE NMR/NQR SPECTROMETER", Rev. Sci. Instrum. 60(10), October 1989, pages 3249–3252, which is incorporated herein by reference.

Therefore, it is known that specific piezoelectric resonance signals occur in various common materials when the materials are irradiated with an electric field. For example, it is known that "sand" produces a piezoelectric resonance signal when irradiated with an electric field.

Although the phenomenon of piezoelectric resonance is known, it does not appear to be conventionally known to screen a plurality of samples for a piezoelectric resonance signal, to determine which of the samples may include a target material.

Therefore, according to embodiments of the present invention, as described in more detail below, a sample includes a target material having a unit cell structure lacking an inversion center of symmetry. For example, the target material is cocaine hydrochloride. AC electric field is applied to the sample to induce a piezoelectric resonance in the target material. The induced piezoelectric resonance is detected, to thereby detect the presence of the target material in the sample.

Figure 2:
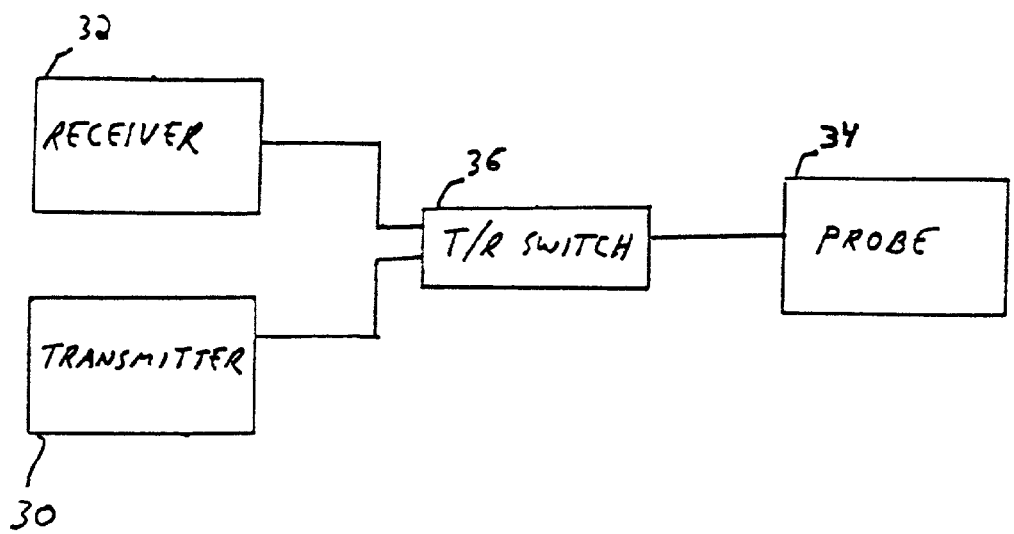
FIG. 2 (prior art) is a diagram illustrating a conventional apparatus for detecting a piezoelectric resonance signal in a sample.

FIG. 2 is a diagram illustrating a conventional apparatus for detecting a piezoelectric resonance signal in a sample. Referring now to FIG. 2, a transmitter 30 and a receiver 32 are connected to a probe 34 through a transmit/receive (T/R) switch 36. To detect the presence of a target material in the sample, T/R switch 36 connects transmitter 30 to probe 34 while disconnecting receiver 32 from probe 34. Then, transmitter 30 generates a pulse and supplies the pulse to probe 34. The pulse is typically of a duration of between 1–1000 μs. Probe 34 receives the pulse and accordingly produces an electric field which is applied to the sample. If the sample includes the target material, the applied electric field will induce a piezoelectric resonance signal in the target material. Depending on the frequency of the applied electric field and the acoustical loss of the sample, the piezoelectric resonance signal can persist on the order of, for example, one millisecond.

After the electric field is applied to the sample by probe 34, T/R switch 36 connects receiver 32 to probe 34 while disconnecting transmitter 30 from probe 34. Therefore, at this time, the applied electric field is turned OFF. If a piezoelectric resonance signal was induced in the target material, probe 34 detects the piezoelectric resonance signal and produces a corresponding output signal. The output signal of probe 34 is received and analyzed by receiver 32. Therefore, T/R switch 36 must be controlled so that probe 34 receives the piezoelectric resonance signal before the piezoelectric resonance signal is dissipated. The irradiation of a sample with an electric field and the detection of a piezoelectric resonance signal can be rapidly repeated to improve the signal-to-noise-ratio.

Preferably, a known pulse approach is used to irradiate a sample with an electric field. Alternatively, a continuous wave approach can be used. There are also obvious and possible useful variations, such as a known swept frequency approach or a multiple frequency irradiation approach.

FIG. 3(A) is a diagram illustrating a probe, for use as probe 34. Referring now to FIG. 3(A), probe 34 includes a coil 37 and a capacitor 38. Coil 37 produces a fringe electric field. Capacitor 38 is formed of two plates 38a and 38b. To be exposed to an electric field produced by probe 34, a sample should be positioned in the fringe electric field of coil 37. Therefore, as illustrated in FIG. 3(A), coil 37 is relatively large, and a sample (such as a suitcase) can be positioned inside coil 37.

Probe 34 typically includes an optional capacitor 42 and a coil 44, which form a resonant circuit with coil 37 and capacitor 38. To produce a piezoelectric resonance signal in a target material, the circuit impedance of the resonant circuit is made real by tuning one of coils 44 and 36 and/or one of capacitors 38 and 42 to a frequency of the order of, for example, 0.1–10 MHz. The impedance of this tuned circuit can be matched or mismatched to the impedance of receiver 32 or transmitter 30, as appropriate. For example, capacitor 42 and coil 44 can provide proper impedance matching between receiver 32 and probe 34, and between transmitter 30 and probe 34. Further, it may be appropriate to use an untuned coil or untuned capacitor in the resonant circuit.

Figure 3B:
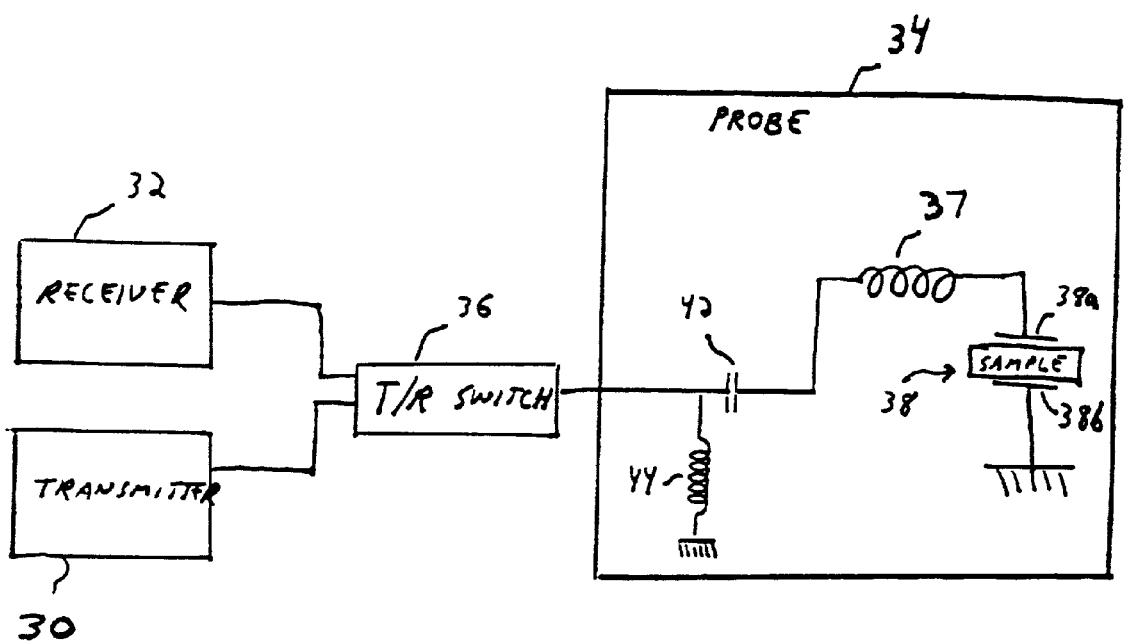
FIG. 3(B) is a diagram illustrating a probe for use in the apparatus of FIG. 2, according to an embodiment of the present invention.

FIG. 3(B) is a diagram illustrating a probe, according to an embodiment of the present invention. Referring now to FIG. 3(B), capacitor 38 is relatively large and produces an electric field between plates 38a and 38b. Therefore, a sample can be positioned between plates 38a and 38b of capacitor 38, as illustrated in FIG. 3(B).

There are many different types of probe designs which can be used, and the present invention is not intended to be limited to a specific probe design. In addition, various designs for transmitter 30 and receiver 30 are well-known.

While the apparatus illustrated in FIG. 2 is known, the present invention relates to the use of the apparatus to detect a target material, where the target material has a unit cell with a cell structure lacking an inversion center of symmetry. It does not appear to be conventionally known to use the apparatus in FIG. 2 to detect a target material having a unit cell with a cell structure having an inversion center of symmetry. Therefore, it does not appear to be conventionally known to use piezoelectric resonance to detect contraband materials such as cocaine hydrochloride, Moreover, according to the embodiments of the present invention, the apparatus in FIG. 2 is used to screen a plurality of samples to determine which of the samples produce a piezoelectric resonance signal, thereby indicating which samples may include a target material. It does not appear to be conventionally known to use the apparatus in FIG. 2 to screen a plurality of samples to determine which of the samples may include the target material.

Figure 4:
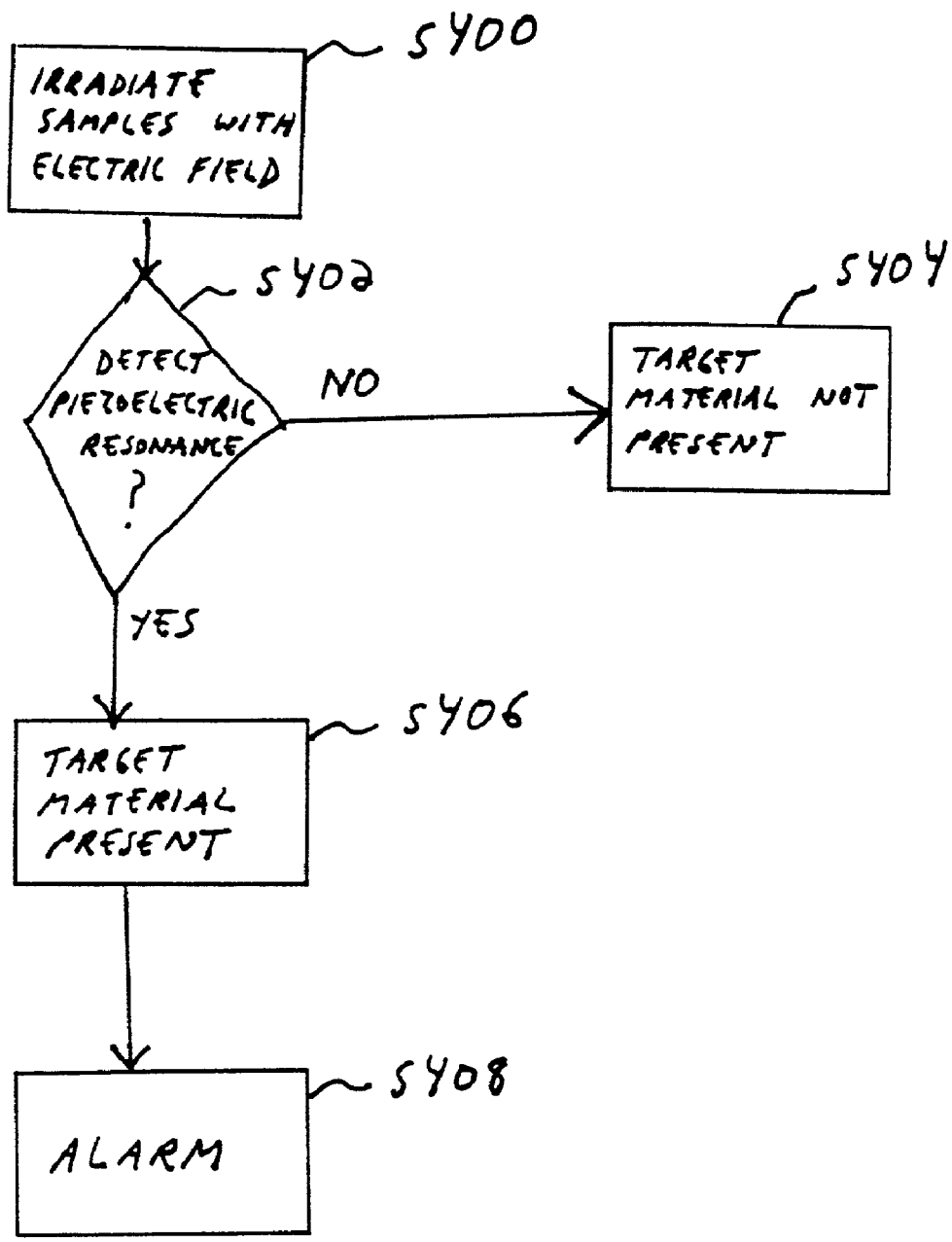
FIG. 4 is a flow chart illustrating a process for screening a plurality of samples to determine which of the samples include a target material, according to an embodiment of the present invention.

FIG. 4 is a flow chart illustrating a process for screening a plurality of samples to determine which of the samples include the target material, according to an embodiment of the present invention. Referring now to FIG. 4, in step S400, each sample is irradiated with an electric field which induces a piezoelectric resonance signal in the target material. More specifically, referring to FIG. 2, T/R switch 36 connects transmitter 30 to probe 34 to irradiate a sample with an electric field. If the sample includes the target material, the electric field will induce a piezoelectric resonance signal in the target material.

From step S400, the process moves to step S402, where it is determined whether a piezoelectric resonance signal was induced by the electric field. More specifically, referring to FIG. 2, T/R switch 36 connects receiver 32 to probe 34 to detect an induced piezoelectric resonance signal.

If an induced piezoelectric resonance signal is not detected or is below a predetermined threshold level in step S402, the process moves to step S404, thereby indicating a high probability that the sample does not include the target material.

If an induced piezoelectric resonance signal is detected in step S402 or is above a predetermined threshold level, the process moves to step S406, thereby indicating a high probability that the sample includes the target material. From step S406, the process moves to step S408, to set off an alarm.

Therefore, for example, the above embodiments of the present invention can be used in ports of entry to search luggage (that is, "samples") for cocaine hydrochloride (that is, a "target material"). If an electric field induces a piezoelectric resonance signal in the luggage, an alarm can be set off to indicate that there is a high probability that the luggage includes cocaine hydrochloride.

Moreover, piezoelectric resonance can be used to "prescreen" samples to determine which of the samples indicate the presence of a target material. Then, each sample indicating the presence of the target material can be further screened by a different process to confirm the presence of the target material in the sample. For example, after a piezoelectric resonance signal indicates the presence of a target material in a sample, the sample can be further screened with nuclear quadrupole resonance (NQR), nuclear magnetic resonance (NMR), canine inspection, or simply by a visual inspection, to confirm whether or not the sample includes the target material.

Figure 5:
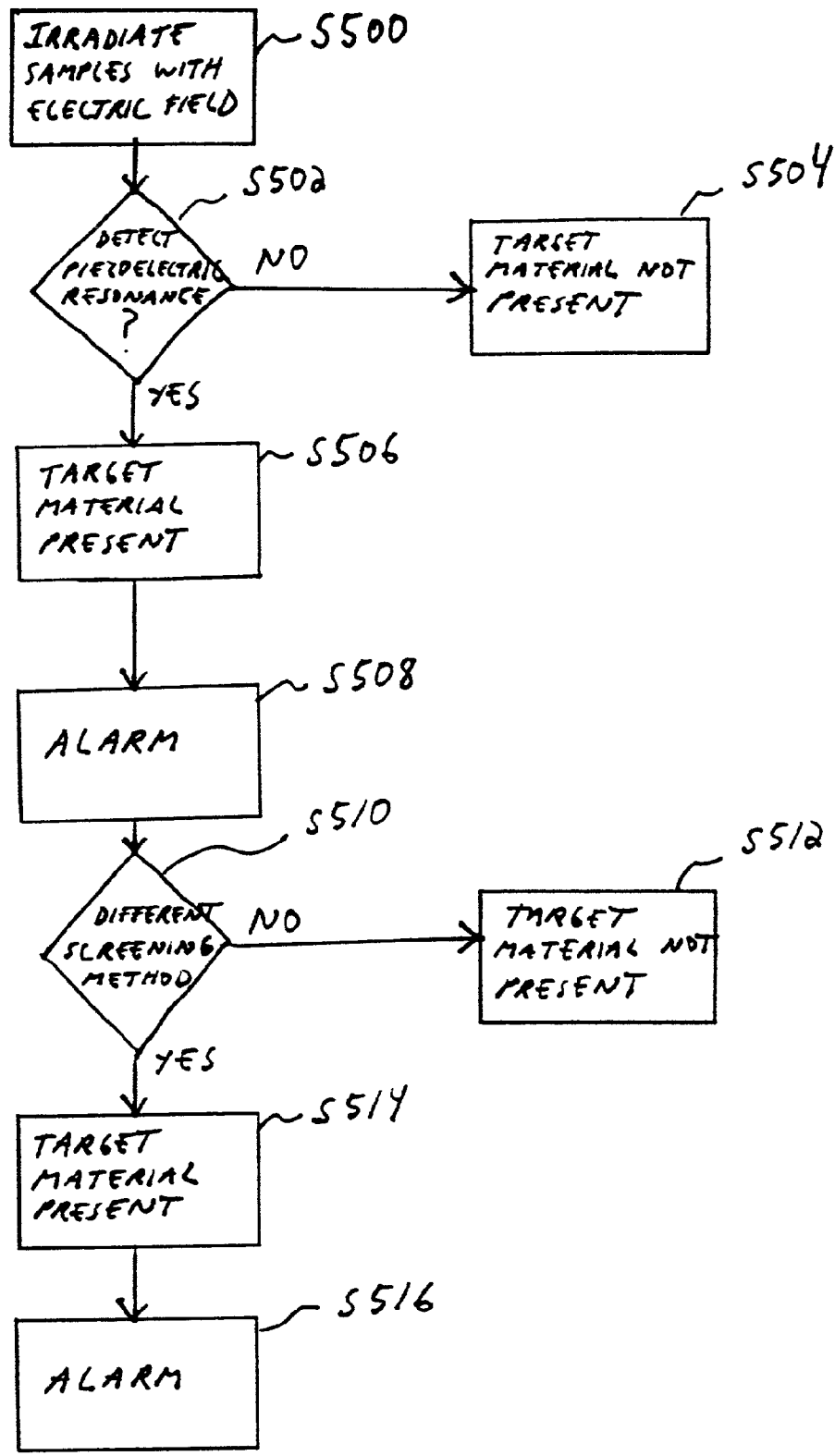
FIG. 5 is a flow chart illustrating a process for screening a plurality of samples to determine which of the samples include a target material, according to an additional embodiment of the present invention.

For example, FIG. 5 is a flow chart illustrating a process for screening a plurality of samples to determine which of the samples include the target material, according to an additional embodiment of the present invention. Referring now to FIG. 5, in step S500, each sample is irradiated with an electric field which induces a piezoelectric resonance signal in the target material. More specifically, referring to FIG. 2, T/R switch 36 connects transmitter 30 to probe 34 to irradiate a sample with an electric field. If the sample includes the target material, the electric field will induce a piezoelectric resonance signal in the target material.

From step S500, the process moves to step S502, where it is determined whether a piezoelectric resonance signal was induced by the electric field. More specifically, referring to FIG. 2, T/R switch 36 connects receiver 32 to probe 34 to detect an induced piezoelectric resonance signal.

If an induced piezoelectric resonance signal is not detected in step S502 or is below a predetermined threshold level, the process moves to step S504, thereby indicating a high probability that the sample does not include the target material.

If an induced piezoelectric resonance signal is detected in step S502 or is above a predetermined threshold level, the process moves to step S506, thereby indicating a high probability that the sample includes the target material. From step S506, the process moves to step S508, to set off an alarm. Once the alarm is set off in step S508, the sample can be, for example, set aside for further screening.

From step S508, the process moves to step S510, where a different process (that is, a process different from the detection of piezoelectric resonance) is used to further screen the samples for which an induced piezoelectric resonance signal was detected. For example, in step S510, nuclear quadrupole resonance (NQR), nuclear magnetic resonance (NMR), or simply a visual inspection can be performed, to confirm whether or not the sample includes the target material. If NQR or NMR is performed, an apparatus as illustrated, for example, in FIG. 1, can be used.

If the screening process performed in step S510 does not indicate the presence of the target material, the process moves to step S512, thereby indicating a high probability that the sample does not include the target material.

If the screening process performed in step S510 indicates the presence of the target material, the process moves to step S514, thereby indicating a very high probability that the sample includes the target material. From step S514, the process moves to step S516, to set off an alarm.

According to the above embodiments of the present invention, an apparatus determines which samples of a plurality of samples include a target material, wherein the target material has first and second characteristics. The first characteristic is that the target material has a piezoelectric resonance signal when irradiated with an electric field. The second characteristic can be, for example, a visual or olfactory characteristic, or that the target material has a specific nuclear quadrupole resonance when irradiated with an electromagnetic field. The apparatus includes a first characteristic determining unit and a second characteristic determining unit. The first characteristic determining unit determines which samples indicate the presence of the first characteristic, to thereby determine which samples indicate the presence of the target material. For example, the apparatus illustrated in FIG. 2 operates as the first characteristic determining unit. The second characteristic determining unit determines, for each sample determined to indicate the presence of the first characteristic by the first characteristic determining unit, which of the samples indicate the presence of the second characteristic, to thereby confirm which samples include the target material. For example, the apparatus illustrated in FIG. 1 operates as the second characteristic determining unit.

According to the above embodiments of the present invention, an apparatus includes a piezoelectric resonance determination unit and a nuclear quadrupole resonance determination unit. The piezoelectric resonance determination unit determines which samples have a piezoelectric resonance signal when irradiated with an electric field. For example the apparatus illustrated in FIG. 2 operates as the piezoelectric resonance determination unit. The nuclear quadrupole resonance determination unit, for each sample determined to have the piezoelectric resonance signal, determines which of the samples have a specific nuclear quadrupole resonance when irradiated with an electromagnetic field. For example, the apparatus illustrated in FIG. 1 operates as the nuclear quadrupole resonance determination unit.

The term "piezoelectric resonance" is used herein. However, it should be appreciated that resonance frequencies depend on the sample geometry as well as the intrinsic features of the molecular structure of the target material (i.e., the lack of a crystallographic inversion center and the presence of the polarizable groups).

An apparatus for detecting a piezoelectric resonance signal (such as the apparatus illustrated in FIG. 2), is generally much less sophisticated and much less expensive than a conventional apparatus for detecting NQR or NMR. Also, detecting a piezoelectric resonance signal generally provides a higher sensitivity and faster detection than conventional apparatus for detection of NQR or NMR. Generally, these advantages are due to the stronger piezoelectric resonance signal. Therefore, by detecting piezoelectric resonance, or by pre-screening for piezoelectric resonance, the embodiments of the present invention can provide many advantages over the sole detection of NQR or NMR.

For example, by pre-screening for piezoelectric resonance, a large number of samples can be quickly screened. Only those samples exhibiting a piezoelectric resonance are further scanned. Therefore, for example, an airport luggage-scanning process can proceed relatively rapidly without subjecting every piece of luggage to a slower NQR screening.

Further, a transmitter, receiver and probe used in an apparatus for detecting piezoelectric resonance (such as the apparatus illustrated in FIG. 2) can be made of essentially the same components as those used in an NQR or NMR apparatus (such as the apparatus illustrated in FIG. 1). Generally, the frequencies and durations of pulses produced by a transmitter may be different, and the time period for switching a T/R switch may be different. Therefore, a common transmitter, a common receiver, a common T/R switch, and/or a common probe can typically be used to pre-screen for piezoelectric resonance, and to further screen for NQR and/or NMR. However, the transmitter should be capable of producing different types of pulses, and the receiver should be capable of receiving and analyzing different types of signals. It should be noted, however, that the physical basis of the response for piezoelectric resonance is entirely different from that of NQR and NMR.

Although FIGS. 1 and 2 illustrate a transmitter and a receiver connected to a common probe through a T/R switch, separate transmit and receive systems could easily be employed. For example, a transmitter could have a dedicated probe connected thereto for transmitting an electric field or an electromagnetic field towards a sample, and a receiver could have a dedicated probe connected thereto for receiving a resonance signal from the sample. In this case, a T/R switch would not be necessary.

According to the above embodiments of the present invention, a "sample" includes a target material. Thus, for example, a "sample" can be a material which has the target material mixed therein. Alternatively, for example, a "sample" can be a piece of luggage or mail having the target material therein. A "sample" could also be, for example, an article of clothing having the target material in a pocket or sewn in a lining. Therefore, there are many different types of "samples", and the present invention is not intended to be limited to any specific type.

It is often desirable to add identifying tags to a material, so that the origin of the material can be identified. For example, it is known that tags can be added to an explosive material by the manufacturer of the explosive material. Then, if the explosive material is used, for example, in an a bomb, tags from the explosive residue can be analyzed to trace the origin of the bomb. Therefore, the use of tags can be of great assistance to law enforcement personnel. Furthermore, tags may be added to an explosive material to identify the source of undetonated explosives.

Conventionally, various types of tags are known. For example, volatile solvents which can be detected by vapor detection can be used as tags. In addition, it is conventionally known that x-ray fluorescents, colored plastic chips, and radioactive materials can be used as tags.

However, the present invention recognizes that the principle of piezoelectric resonance can be used to detect tags. Therefore, according to embodiments of the present invention, a material which produces a strong and specific piezoelectric resonance when irradiated with an electric field is used as a tag. This material may be produced by controlling the particle size and shape. Then, when the origin of the material is to be determined, the material can be irradiated with an electric field to find and identify the tag.

Since different materials and different shapes produce different piezoelectric resonance signals, manufacturers of controlled materials might use a slightly different material as a tag, or a combination of materials to provide a fingerprint. In this manner, the nature or origin of manufacture of a specific material can easily be determined by irradiating a sample of the material with an electric field to discover the tag.

Figure 6:
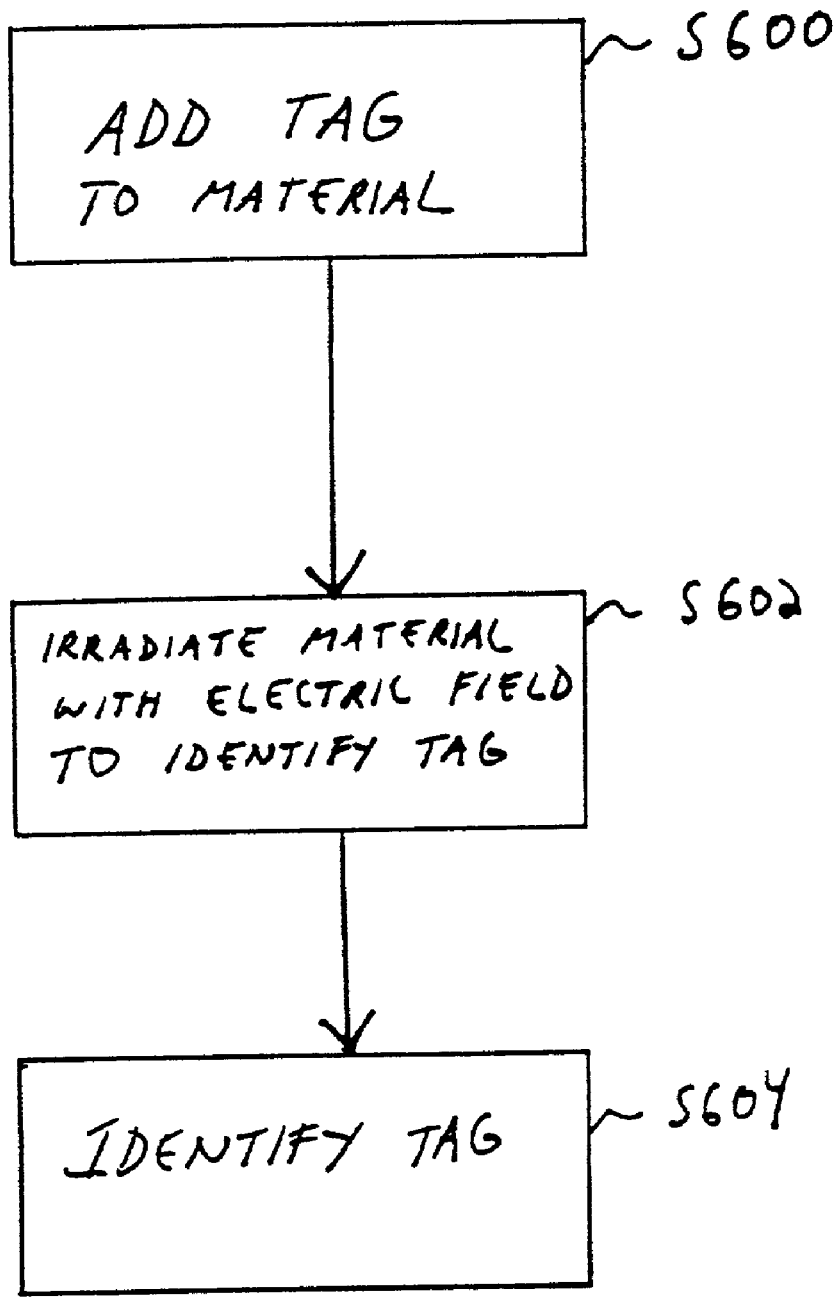
FIG. 6 is a flow chart illustrating a process for using tags to identify the origin of a material, according to an embodiment of the present invention.

FIG. 6 is a flow chart illustrating a process for using tags to identify the origin of a material, according to an embodiment of the present invention. Referring now to FIG. 6, in step S600, a tag is added to a material, such as an explosive material. The tag produces a specific piezoelectric resonance signal when irradiated with an electric field. From step S600, the process moves to step S602, where the material is irradiated with an electric field to cause the tag to produce the piezoelectric resonance signal. From step S602, the process moves to step S604, where the tag is identified from the piezoelectric resonance signal. Of course, steps S600, S602 and S604 can be performed at significantly different time periods. For example, step S600 would typically be performed when the material is being manufactured. By contrast, step S602 would typically be performed when the material is found at a later date, such as when the material is found in bomb residue of an exploded bomb.

Further, the use of tags, as described herein, is not intended to be limited solely to detecting the manufacture of a material. There are many other uses for adding tags to a material: merchandise security, libraries, factory production monitoring, etc.

As noted above, there are many materials which produce a piezoelectric resonance when irradiated with an electric field, and the embodiments of the present invention are not intended to be limited to any specific material.

Therefore, according to the above embodiments of the present invention, a method includes the steps of: (a) adding a tag to a material, the tag producing a piezoelectric resonance signal when irradiated with an electric field, (b) irradiating the material with an electric field to cause the tag to produce the piezoelectric resonance, thereby identifying the tag. The material can be an explosive material, and the tag can identify a manufacturer of the material.

Although a few preferred embodiments of the present invention have been shown and described, it would be appreciated by those skilled in the art that changes may be made in these embodiments without departing from the principals and spirit of the invention, the scope of which is defined in the claims and their equivalents.

What is claimed is:

1. A probe comprising:
   a capacitor including first and second plates separated from each other with an electric field being formed between the first and second plates, wherein a sample is positioned between the first and second plates so that the electric field induces a piezoeletric resonance signal in the sample and so that the probe detects the induced piezoeletric resonance signal.

2. A probe as in claim 1, further comprising:
   an inductor which, together with the capacitor, forms a tuned circuit having a piezoeletric resonance frequency which determines a frequency of the electric field formed between the first and second plates.

3. A probe as in claim 1, wherein the first and second plates of the capacitor are parallel to each other.

4. A probe as in claim 2, wherein the first and second plates of the capacitor are parallel to each other.

* * * * *